(12) United States Patent
Velings et al.

(10) Patent No.: US 6,368,610 B1
(45) Date of Patent: Apr. 9, 2002

(54) DISINFECTING COMPOSITION

(75) Inventors: Nicolas Velings, Braine-L'Alleud; Ferdinand Herman, Deinze; Paul-Eric Loncin, Sint-Pieters Leeuw, all of (BE)

(73) Assignee: SOPURA S.A., Courcelles (BE)

( * ) Notice: Subject to any disclaimer, the term of this patent is extended or adjusted under 35 U.S.C. 154(b) by 0 days.

(21) Appl. No.: 09/485,239

(22) PCT Filed: Aug. 5, 1998

(86) PCT No.: PCT/BE98/00119
§ 371 Date: Feb. 7, 2000
§ 102(e) Date: Feb. 7, 2000

(87) PCT Pub. No.: WO99/07222
PCT Pub. Date: Feb. 18, 1999

(30) Foreign Application Priority Data

Aug. 5, 1997 (BE) ............................................. 9700663

(51) Int. Cl.$^7$ ................................................ A01N 25/02
(52) U.S. Cl. ................ 424/405; 424/406; 424/605; 424/709; 424/718; 514/557; 514/558; 514/560; 514/722; 514/723; 510/199; 510/218; 510/219; 510/234
(58) Field of Search ................................. 514/557, 558, 514/560, 722, 723; 510/199, 218, 219, 234; 424/405, 406, 605, 709, 718

(56) References Cited

U.S. PATENT DOCUMENTS 5,391,379 A    2/1995   McKinzie et al.   .......... 424/605

FOREIGN PATENT DOCUMENTS

| EP | 0 147 102 A2 | 7/1985 | .......... A01N/59/26 |
| EP | 0 245 928 A2 | 11/1987 | .......... A01N/37/02 |
| EP | 0524075 | 1/1993 | |
| WO | 83/00163 | 1/1983 | ............ C11D/3/48 |
| WO | 86/05510 | 9/1986 | ............ C11D/1/72 |
| WO | 94/10837 | 5/1994 | .......... A01N/25/00 |
| WO | 96/11572 | 4/1996 | .......... A01N/37/02 |

*Primary Examiner*—Neil S. Levy
(74) *Attorney, Agent, or Firm*—Venable; George H. Spencer; Ashley J. Wells

(57) ABSTRACT

A disinfecting composition which is bactericidal and effective to kill yeast includes (a) at least one a monocarboxylic acid of formula R—COOH, in which R a saturated or unsaturated, straight- or branched-chain alkyl radical comprising from 6 to 12 carbon atoms; (b) a strong inorganic acid; (c) at least one organic acid of formula R'CH$_2$—CO$_2$H, in which R' is H or OH; (d) at least one anionic surfactant; (e) at least one solubilizing agent consisting of a compound of formula R"O(CH$_2$CH$_2$O)$_x$—H, in which R" represents a C$_2$ to C$_6$ alkyl radical, x represents an integer from 1 to 3; and (f) water.

25 Claims, No Drawings

DISINFECTING COMPOSITION

BACKGROUND OF THE INVENTION

1. Field of the Invention

A subject matter of the present invention is a cleaning and disinfecting composition of particular use in the cleaning and disinfecting of pipes and vessels of plants in the food industry, in particular the brewing industry, dairy industry, and the like.

2. Description of the Related Art

Compositions for cleaning and disinfecting plants in the farm produce industries are mainly used in systems known as "cleaning in place" (CIP) systems, according to which the plant is cleaned and disinfected without being disassembled, the disinfecting cleaning composition being circulated in the plant by pumping and/or applied by spraying (by means of permanently installed sprayers), so as to reach all parts of the plant to be treated.

In order to be applicable in a truly satisfactory manner in the food industry and more particularly in the brewing industry, such a disinfecting composition must combine several properties and must meet several requirements which it is difficult to satisfy simultaneously.

A solution for use prepared by dilution of such a composition must in particular have a satisfactory microbiocidal action, both with regard to gram+ and gram− bacteria and with regard to yeasts, such as Saccharomyces, Candida, and the like. A satisfactory microbiocidal effect is considered to have been obtained when the initial population of microorganisms is reduced by a factor of $10^5$ in less than 20 minutes at 3° C.

Such a solution for use must also be non-foaming or, in any case, exhibit very little foaming. This is because the formation of foam can result in cavitation of the pumps of the CIP system, causing non-circulation of the disinfecting solution and possibly destroying the pumps. In addition, the formation, even modest, of foam can result in difficulties during rinsing.

Such a solution for use must also have a good cleaning and optionally descaling power and be fully rinsable, that is to say without risk of specific adsorption on the surfaces of the materials commonly encountered in plants in the food industry.

The concentrated composition must be stable and homogeneous.

The solution for use prepared by dilution of this concentrated composition must also itself be homogeneous and sufficiently stable to allow it be recovered. This is because the solutions for use used in a CIP system are recovered after use and collected in storage tanks in order to be reused during a subsequent cleaning and disinfection operation on the plant.

Before a fresh use of a recovered solution for use, the concentration of this solution should generally be readjusted by the addition of a certain amount of the concentrated composition. It is consequently important for the concentration of the solution for use to be able to be easily measured continuously. When the solution for use comprises a constituent such as a strong acid, the concentration of active constituents in the solution is very easily measured by measuring the electrical conductivity of the solution, since this conductivity is approximately proportional to the concentration of strong acid, which concentration is proportional to that of the other active constituents of the solution for use.

Numerous compositions for cleaning and/or disinfecting plants in the agricultural and food industries have already been provided.

EP-A-0,147,102 discloses an antimicrobial composition comprising an inorganic acid and/or an organic acid, an α-halogenated acetic acid and a linear or branched aliphatic fatty acid.

An antimicrobial composition which essentially comprises an aliphatic alcohol having from 6 to 12 carbon atoms and an aliphatic acid having from 2 to 6 carbon atoms, which acid is substituted at the α-position by a chloro, iodo, cyano, nitro, amino, imino, thiohydroxyl or hydroxyl radical, is known from EP-A-0,208,403. This composition can also comprise an organic or inorganic acid.

EP-A-0,524,075 discloses a disinfecting acid composition based on phosphoric acid and optionally on hydroxyacetic acid comprising a specific nonionic surface-active agent and an anionic hydrotropic agent of the arylsulfonate or alkylsulfonate type.

A dilutable disinfecting cleaning composition comprising a fatty acid, a hydrotropic agent of the type of surface-active sulfonates, a strong acid and a stabilizing agent consisting of propionic acid, butyric acid, valeric acid or a mixture of these acids, is known from WO 94/10837.

Disinfecting and cleaning compositions for the food industry are known from the document EP-A-0,245,928, these compositions comprising a monocarboxylic or dicarboxylic acid, a solubilizing agent, a diluent and an acid or a mixture of acids, in order to ensure a pH of less than 5. As specified in the document EP-B-0,245,928, the solubilizing agent must be an agent of the alkylated N,N-dimethylamine oxide type with 8 to 10 carbon atoms in the alkyl part in order for the composition to be stable and not very foaming.

SUMMARY OF THE INVENTION

It has now been found that compositions not comprising this solubilizing agent are stable and not very foaming and have an excellent effectiveness in combating bacteria and yeast. Furthermore, the compositions according to the invention can be easily discharged from the vessels and pipes by rinsing, so that any risk of detrimental change in the taste or flavor of the foodstuff by the presence of traces of compositions according to the invention can be avoided. The compositions according to the invention are therefore fungicidal and bactericidal compositions of low toxicity.

The disinfecting composition according to the invention, which is provided either in concentrated form or in dilute form, is a liquid composition comprising:

(a) a monocarboxylic acid of formula

with R a saturated or unsaturated, straight- or branched-chain alkyl radical comprising from 6 to 12 carbon atoms (preferably from 8 to 10 carbon atoms), or a mixture of such carboxylic acids;

(b) a strong inorganic acid, (c) an organic acid of formula:

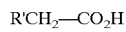

with R': H or OH, or a mixture of such organic acids;

(d) one or more anionic surfactants;
(e) a solubilizing agent consisting of a compound of formula:

$$R''O(CH_2CH_2O)_x—H$$

in which
R'' represents a $C_2$ to $C_6$ alkyl radical,
x represents an integer from 1 to 3, or a mixture of such compounds;
(f) water.

The composition according to the invention is a bactericidal and fungicidal composition.

According to one embodiment of the concentrated composition, it comprises:
(a) from 0.25 to 20% by weight of a monocarboxylic acid of formula:

$$R—COOH$$

with R a saturated or unsaturated, straight- or branched-chain alkyl radical comprising from 6 to 12 carbon atoms, or of a mixture of such carboxylic acids;
(b) from 20 to 40% by weight of a strong inorganic acid;
(c) from 0.25 to 7% by weight of an organic acid of formula:

$$R'CH_2—CO_2H$$

with R': H or OH,
or from 0.5 to 12% by weight of a mixture of such organic acids;
(d) from 5 to 20% by weight of anionic surfactant(s), and
(e) from 1 to 10% by weight of a solubilizing agent consisting of a compound of formula:

$$R''O(CH_2CH_2O)_x—H$$

in which
R'' represents a $C_3$ to $C_5$ alkyl radical,
x represents an integer from 1 to 3, or a mixture of such compounds.

In a particularly advantageous way, the composition comprises:
(a) from 0.5 to 15% by weight of a monocarboxylic acid of formula:

$$R—COOH$$

with R a saturated or unsaturated, straight- or branched-chain alkyl radical comprising from 6 to 12 carbon atoms, or of a mixture of such carboxylic acids;
(b) from 25 to 35% by weight of a strong inorganic acid;
(c) from 2 to 5% by weight of an organic acid of formula:

$$R'CH_2—CO_2H$$

with R': H or OH,
or from 5 to 10% by weight of a mixture of such organic acids;
(d) from 7 to 13% by weight of anionic surfactant(s), and
(e) from 3 to 7% by weight of a solubilizing agent consisting of a compound of formula:

$$R''O(CH_2CH_2O)_x—H$$

in which
R'' represents a $C_2$ to $C_6$ alkyl radical,
x represents an integer from 1 to 3, or a mixture of such compounds.

The strong inorganic acid present in the composition is preferably chosen from sulfuric acid, phosphoric acid and their mixtures.

Use is advantageously made, in the formulation according to the invention, of glycolic acid as organic acid of formula $R'CH_2—CO_2H$ or of a mixture of glycolic acid and acetic acid as mixture of organic acids of formula $R'CH_2—CO_2H$. As advantageous example, the mixture of said organic acids contains from 30 to 70% by weight of glycolic acid and from 70 to 30% by weight of acetic acid.

According to a specific embodiment of the invention, the solubilizing agent is chosen from:
the compound of formula $CH_2(CH_2)_3—O—CH_2CH_2OH$ (2-butoxyethanol or "butyl glycol")
the compound of formula $CH_2(CH_2)_3—O—(CH_2CH_2O)_2H$ (2-(2-butoxyethoxy)ethanol or "butyl diglycol").

In addition, the composition according to the invention advantageously comprises from 0.1 to 1.0% by weight of a nonionic surface-active agent of general formula:

$$R'''O(CH_2CH_2O)_yH$$

in which
R''' is a saturated $C_{16}$ to $C_{18}$ alkyl radical, and
y is an integer between 8 and 40, or a mixture of such nonionic surface-active agents.

This nonionic surface-active agent can consist in particular of a compound of formula:

$$R'''O(CH_2CH_2O)_yH$$

in which
R''' is a saturated $C_{16}$ to $C_{18}$ alkyl radical, and
y is equal to approximately 11.

Such a nonionic surface-active agent is sold, for example, by the firm BASF under the name Lutensol AT 11®.

The composition advantageously comprises from 0.3 to 0.4% by weight of such a nonionic surface-active agent.

The pH of the composition is advantageously less than 5.

According to a specific embodiment, the strong inorganic acid/organic acid(s) of formula $R'CH_2—CO_2H$ ratio by weight is between 2/1 and 5/1.

The organic acid(s) of formula $R'CH_2CO_2H$/monocarboxylic acid(s) of formula R—COOH ratio by weight is advantageously between 3/1 and 10/1.

The organic acid(s) of formula $R'CH_2—CO_2H$/solubilizing agent of formula $R''O—(CH_2CH_2O)_x—H$ ratio by weight is preferably between 3/1 and 1/1.

Use is advantageously made, as anionic surfactant, of a mixture of anionic surfactants, for example a mixture of a sulfonate surfactant, such as an alkylbenzenesulfonate with 8 to 16 carbon atoms, for example cumenesulfonate, and of a sulfonate from the family of the ether carboxylic acids, for example a mixture of ether carboxylic acids comprising from 15 to 25 carbon atoms and corresponding to the following general formula:

$$R''''(OC_2H_4)_nOCH_2COOH$$

with R'''' an alkyl group with 4 to 12 carbon atoms.

The sulfonate surfactant is advantageously chosen from alkylsulfonates with 8 to 16 carbon atoms and the mixtures of these. When use is made of a mixture of sulfonate surfactant and of ether carboxylic acid surfactant, use is made of a mixture containing, for example, from 20 to 80% by weight of sulfonate surfactant and from 80 to 20% by weight of ether carboxylic acid surfactant. However, the mixture advantageously comprises more than 50% by weight of sulfonate surfactant.

Another subject matter of the invention is the use of a composition according to the invention as fungicidal composition, in particular fungicidal and bactericidal composition.

A further subject matter of the invention is a process for disinfecting a plant (pipework), vessels, and the like), in which process a composition according to the invention, preferably in dilute form, is brought into contact with the plant.

The concentrated composition is advantageously diluted so that the solution, after dilution, has a content of strong inorganic acid of less than 0.4% and at pH of less than 4, preferably of less than 3.

Disinfecting is advantageously carried out at a temperature of between 0 and 25° C.

DESCRIPTION OF THE PREFERRED EMBODIMENTS

Examples of embodiments will be described hereinbelow:

Liquid compositions according to the invention were prepared by mixing the following ingredients: capric acid (CA1) and/or caprylic acid (CA2), glycolic acid (50% by weight) and acetic acid (50% by weight) mixture (GA-AA), 100% sulfuric acid (SA), butyl diglycol or 2-(2-butoxyethoxy)ethanol (BG), and surfactant (S), such as a mixture of alkylsulfonates with 8 to 12 carbon atoms (72% by weight), of $C_{15}$ to $C_{25}$ ether carboxylic acids (24% by weight) and of Lutensol AT11® (3% by weight).

The contents by weight of the various ingredients in the various compositions prepared are given in the following table.

|    | CA1 | CA2 | GA-AA | SA  | BG  | S     | WATER |
|----|-----|-----|-------|-----|-----|-------|-------|
| 1  |     | 2   | 10    | 40  | 5.0 | 10.0  | 33.0  |
| 2  | 2   |     | 10    | 40  | 5.0 | 10.0  | 33.0  |
| 3  | 0.5 | 0.5 | 8.4   | 31.2| 5.0 | 11.35 | 43.05 |
| 4  | 0.5 | 0.5 | 20    | 30  | 10  | 10    | 29.0  |

-continued

|    | CA1  | CA2  | GA-AA | SA   | BG  | S     | WATER |
|----|------|------|-------|------|-----|-------|-------|
| 5  | 1.25 | 1.25 | 7.7   | 39   | 5.0 | 11.5  | 34.3  |
| 6  | 2.5  | 2.5  | 10    | 35   | 5.0 | 15    | 30    |
| 7  | 1.5  | 1.5  | 9.7   | 31.2 | 5.0 | 11.35 | 39.75 |
| 8  | 1.5  | 1.5  | 8.4   | 31.2 | 3.0 | 11.5  | 42.9  |
| 9  | 2    | 1.5  | 8.0   | 33.0 | 6.0 | 15    | 34.5  |
| 10 | 1.5  | 1.5  | 8.4   | 31.2 | 5.0 | 10.0  | 42.4  |

These concentrated compositions all had a pH of lees than 5 (pH varying from 0 to 2). Other additives can, if appropriate, be added to these concentrated compositions. The concentrated compositions were non-foaming and stable.

According to embodiments of concentrated compositions according to the invention, glycolic acid alone and acetic acid alone were used instead of a mixture of glycolic acid and acetic acid. However, glycolic acid mixed with acetic acid proved to be the most suitable.

For their use in disinfecting pipes, vessels, and the like, the concentrated compositions were diluted so that the pH of the dilute composition was less than 3. Tests of disinfecting by means of the composition 7 with a degree of dilution of 200 times showed that both bacterial disinfecting and yeast disinfecting were rapid and that the foaming problems were avoided.

FOAM TEST

In order to confirm the non-foaming or non-foam-accumulating nature of formulations according to the invention, a measuring cylinder test and a foam generator test were carried out.

Measuring Cylinder Test:

The procedure is as follows:

A 100 ml measuring cylinder is filled with 50 ml of the solution for use (dilution factor 200×) and it is closed using a stopper.

The measuring cylinder is shaken vigorously 10× and the level of the foam is subsequently recorded every 15 seconds for 1 minute.

The operation is resumed 3× with the same solution in order to confirm whether there is foam accumulation.

|   | Result: | | | | | | | | | | | | | | |
|---|---|---|---|---|---|---|---|---|---|---|---|---|---|---|---|
|   | Test 1 Foam volume (ml) after | | | | | Test 2 Foam volume (ml) after | | | | | Test 3 Foam volume (ml) after | | | | |
|   | 0 | 15 | 30 | 45 | 60 sec | 0 | 15 | 30 | 45 | 60 sec | 0 | 15 | 30 | 45 | 60 sec |
| A | 80 | 75 | 75 | 70 | 70 | 80 | 75 | 75 | 70 | 70 | 80 | 75 | 75 | 70 | 70 |
| B | 80 | 75 | 75 | 70 | 70 | 90 | 90 | 80 | 50 | 75 | 100 | 100 | 100 | 90 | 90 |
| C | 65 | 51 | 50 | 50 | 50 | 60 | 51 | 50 | 50 | 50 | 55 | 50 | 50 | 50 | 50 |
| D | 60 | 51 | 51 | 50 | 50 | 58 | 51 | 51 | 50 | 50 | 55 | 50 | 50 | 50 | 50 |
| E | 55 | 50 | 50 | 50 | 50 | 55 | 50 | 50 | 50 | 50 | 55 | 50 | 50 | 50 | 50 |

A: non-accumulating foaming reference product
B: accumulating foaming reference product
C: formulation 7 diluted 200×
D: formulation 7 diluted 100×
E: non-accumulating non-foaming reference product It emerges from this table that the formulation 7 is not very foaming and is non-accumulating. The foam is even observed to decrease with repetition of the test.

Foam Generator Test:

The principle is as follows:

A solution for use (5 liters) is placed in a stainless steel vessel. The solution is circulated using a pump (throughput: 3000 l/h) through +/−4 meters of pipe (of various diameters), 1 meter of which is filled with a stainless steel wire mesh in order to increase the head losses. The behavior of the solution is observed for 3 periods of 8 hours.

With the exception of a scum on the solution, neither formation of foam nor cavitation of the pump was observed. The formulation 7 therefore has the characteristics of a non-foaming formulation.

TEST OF MICROBIOCIDAL ACTIVITY

Principle of the method.

The measurement method is modeled on the European method recommended by the Council of Europe (Strasbourg 1987): "Test methods for the antimicrobial activity of disinfectants in food hygiene", and on the draft European Standard prEN1276 (December 1993): "Désinfectants et antiseptiques chimiques—Essai quantitatif de suspension pour l'évaluation de l'activité bactéricide des antiseptiques et des désinfectants chimiques utilisés dans le domaine de l'alimentation, dans l'industrie, dans les domaines domestiques et en collectivité" [Chemical antiseptics and disinfectants—Quantitative suspension test for the evaluation of the bactericidal activity of chemical disinfectants and antiseptics used in the field of food, in industry, and in domestic and communal environments].

The principle thereof is as follows:

A microbial suspension is brought into contact, in a water of specific composition (hardness corresponding to 300 ppm of $CaCO_3$) comprising the germicidal product at its concentration of use, for predetermined times (for example, 3, 6 and 12 minutes), at the chosen temperature, 3 or 20° C. Surviving microorganisms are subsequently counted, which makes it possible to determine the time necessary in order to reduce the initial population by a factor of $10^5$.

The results obtained are shown in the following tables:

Microbial Strains Used

| 1. Bacteria | |
|---|---|
| N of the strain | Designation |
| 404 | *Enterobacter cloacae* DSM 3264 |
| 401 | *Enterococcus faecium* ATCC 10541 |
| 204 | *Escherichia coli* ATCC 10536 |
| 403 | *Lactobacillus brevis* DSM 6235 |
| 504 | *Pediococcus damnosus* ATCC 43013 |
| 402 | *Proteus mirabilis* ATCC 14153 |
| 290 | *Pseudomonas aeruginosa* ATCC 15442 |
| 333 | *Staphylococcus aureus* subs. Aureus ATCC 6536 |

| 2. Yeasts | |
|---|---|
| N of the strain | Designation |
| 386 | *Candida albicans* ATCC 10231 |
| 247 | *Saccharomyces cerevisiae* ATCC 9763 |
| 196 | *Saccharomyces cerevisiae* (diastaticus) CBS 1782 |

Extermination times observed.

The time (in minutes) required in order to reduce by a factor of $10^5$, at temperatures of 20 and 3° C., with a concentration of the composition of 1.0 vol % and of 0.5 vol %, is given in the following table:

| Temp.-> | 20° C. | | 30° C. | |
|---|---|---|---|---|
| conc.-> | 1.0 vol % | 0.5 vol % | 1.0 vol % | 0.5 vol % |
| Strain | | | | |
| 404 | <5.0 | <5.0 | <5.0 | <5.0 |
| 401 | <5.0 | <5.0 | <5.0 | 5.7 |
| 204 | <5.0 | <5.0 | <5.0 | <5.0 |
| 403 | <5.0 | <5.0 | <5.0 | <5.0 |
| 504 | <5.0 | <5.0 | <5.0 | <5.0 |
| 402 | <5.0 | <5.0 | <5.0 | <5.0 |
| 290 | <5.0 | <5.0 | <5.0 | <5.0 |
| 333 | <5.0 | <5.0 | <5.0 | <5.0 |
| 386 | <5.0 | <5.0 | <5.0 | 6 |
| 247 | <5.0 | <5.0 | 9 | 11 |
| 196 | <5.0 | <5.0 | 5.1 | 9 |

The composition 7 can therefore be regarded as bactericidal and yeast-killing.

What is claimed is:

1. A disinfecting composition which is at least one of bactericidal and fungicidal, comprising:
   (a) at least one monocarboxylic acid of formula R—COOH, in which R a saturated or unsaturated, straight- or branched-chain alkyl radical comprising from 6 to 12 carbon atoms;
   (b) an inorganic acid;
   (c) at least one organic acid of formula $R'CH_2$—$CO_2H$, in which R' is H or OH;
   (d) at least one anionic surfactant;
   (e) at least one solubilizing agent consisting of a compound of formula $R''O(CH_2CH_2O)_xH$, in which R" represents a $C_2$ to $C_6$ alkyl radical and x represents an integer from 1 to 3; and
   (f) water.

2. The disinfecting composition according to claim 1, comprising, based on total weight of the disinfecting composition:
   (a) from 0.25 to 20% by weight of the at least one monocarboxylic acid;
   (b) from 20 to 40% by weight of the strong inorganic acid;
   (c) from 0.25 to 7% by weight of one of the at least one organic acid or from 0.5 to 12% by weight of a mixture of the at least one organic acids;
   (d) from 5 to 20% by weight of the at least one anionic surfactant, and
   (e) from 1 to 10% by weight of the at least one solubilizing agent.

3. The disinfecting composition according to claim 1, comprising, based on total weight of the disinfecting composition:
   (a) from 0.5 to 15% by weight of the at least one monocarboxylic acid;
   (b) from 25 to 35% by weight of the strong inorganic acid;
   (c) from 2 to 5% by weight of the at least one organic acid;
   (d) from 7 to 13% by weight of the at least one anionic surfactant, and
   (e) from 3 to 7% by weight of the at least one solubilizing agent.

4. The disinfecting composition according to claim 1, wherein the inorganic acid is selected from the group consisting of sulfuric acid, phosphoric acid and their mixtures.

5. The disinfecting composition according to claim 4, wherein the inorganic acid is sulfuric acid.

6. The disinfecting composition according to claim 1, wherein the at least one organic acid is a mixture of organic acids of formula $R'CH_2-CO_2H$ and contains, based on total weight of the disinfecting composition, from 30 to 70% by weight of glycolic acid and from 70 to 30% by weight of acetic acid.

7. The disinfecting composition according to claim 1, wherein the at least one solubilizing agent is selected from the group consisting of a compound of formula $CH_3(CH_2)_3-O-CH_2-CH_2OH$ (butyl glycol), a compound of formula $CH_3(CH_2)_3-O-(CH_2CH_2O)_2H$ (butyl diglycol), and mixtures of these compounds.

8. The disinfecting composition according to claim 1, further comprising from 0.1 to 1.0% by weight, based on total weight of the disinfecting composition, of at least one nonionic surface-active agent of general formula $R'''O(CH_2CH_2O)_yH$, in which $R'''$ is a saturated $C_{16}$ to $C_{18}$ alkyl radical and y is an integer between 8 and 40.

9. The disinfecting composition according to claim 8, wherein the at least one nonionic surface-active agent is a compound of general formula $R'''O(CH_2CH_2O)_yH$, in which $R'''$ is a saturated $C_{16}$ to $C_{18}$ alkyl radical, and y is equal to about 11.

10. The disinfecting composition according to claim 8, wherein the at least one nonionic surface-active agent is present in an amount ranging from 0.3 to 0.4% by weight.

11. The disinfecting composition according to claim 1, wherein the disinfecting composition has a pH of less than 5.

12. The disinfecting composition according to claim 11, wherein the disinfecting composition has a pH which does not exceed 2.

13. The disinfecting composition according to claim 1, wherein the disinfecting composition has a weight ratio of the strong inorganic acid to the at least one organic acid which ranges from 2/1 to 5/1.

14. The disinfecting composition according to claim 1, wherein the disinfecting composition has a weight ratio of the at least one organic acid to the at least one monocarboxylic acid which ranges from 3/1 to 10/1.

15. The disinfecting composition according to claim 1, wherein the disinfecting composition has a weight ratio of the at least one organic acid to the at least one solubilizing agent which ranges from 3/1 to 1/1.

16. The disinfecting composition according to claim 1, wherein the at least one anionic surfactant is a mixture of anionic surfactants which comprise at least one surface-active sulfonate and at least one surface-active ether carboxylic acid.

17. The disinfecting composition according to claim 16, wherein the at least one anionic surfactant comprises at least one alkybenzenesulfonate having from 8 to 16 carbon atoms.

18. The disinfecting composition according to claim 16, wherein the at least one anionic surfactant comprises at least one alkylsulfonate having from 8 to 16 carbon atoms.

19. The disinfecting composition according to claim 16, wherein the at least one anionic surfactant comprises a mixture of ether carboxylic acids comprising from 15 to 25 carbon atoms and corresponding to general formula $R''''(OC_2H_4)_nOCH_2COOH$, in which $R''''$ represents an alkyl group having 4 to 12 carbon atoms.

20. The disinfecting composition according to claim 16, wherein the at least one anionic surfactant is a mixture of anionic surfactants and comprises from 20 to 80% by weight, based on total weight of the disinfecting composition, of at least one surface-active sulfonate and from 80 to 20% by weight of at least one surface-active ether carboxylic acid.

21. The disinfecting composition according to claim 16, wherein the at least one anionic surfactant is a mixture of anionic surfactants and comprises more than 50% by weight of at least one surface-active sulfonate.

22. A process for disinfecting a plant, comprising:
    contacting the plant with the disinfecting composition according to claim 1.

23. The process according to claim 22, further comprising diluting the disinfecting composition to provide a content of the inorganic acid which is less than 0.4% by weight, based on total weight of the disinfecting composition.

24. The process according to claim 22, further comprising diluting the disinfecting composition to a pH of less than 4.

25. The process according to claim 22, further comprising diluting the disinfecting composition to a pH of less than 3.

* * * * *